United States Patent [19]

Islip et al.

[11] 4,379,156

[45] Apr. 5, 1983

[54] HETEROCYCLIC CHEMICALS, THEIR PREPARATION AND USE

[75] Inventors: Peter J. Islip, Sanderstead; Mirjana V. Bogunovic, Bromley, both of England

[73] Assignee: Burroughs Wellcome Co., Research Triangle Park, N.C.

[21] Appl. No.: 218,553

[22] Filed: Dec. 22, 1980

[30] Foreign Application Priority Data

Dec. 21, 1979 [GB] United Kingdom ............... 7944276

[51] Int. Cl.³ .................. C07D 277/38; A61K 31/425
[52] U.S. Cl. ..................................... 424/270; 548/192
[58] Field of Search ........................ 548/192; 424/270

[56] References Cited

U.S. PATENT DOCUMENTS

| | | | |
|---|---|---|---|
| 3,499,907 | 3/1970 | Islip | 548/192 |
| 3,523,122 | 8/1970 | Capps | 548/192 |
| 3,660,417 | 5/1972 | Islip | 548/192 |
| 3,671,650 | 6/1972 | Islip | 548/192 |
| 3,950,351 | 4/1976 | Rossignol et al. | 548/192 |

FOREIGN PATENT DOCUMENTS 709399 5/1965 Canada ............................... 548/192

1245916 9/1971 United Kingdom ............... 548/192

*Primary Examiner*—Mary C. Lee
*Attorney, Agent, or Firm*—Donald Brown

[57] ABSTRACT

Compounds of formula (III):

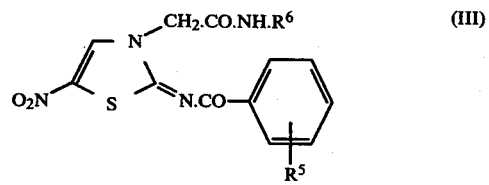

wherein $R^5$ is a single substituent in position 2 or 3 of the phenyl ring and when in the 2-position $R^5$ is a chlorine atom, a methyl group or a nitro group; and $R^6$ is a hydrogen atom or a $CO.CH_3$ group may be prepared by methods analogous to those known in the art, for example, by reaction of the corresponding nitrothiazolyl benzamide with the corresponding halo(di)acetamide. The compounds of formula (III) have schistosomicidal activity and may be administered either as the compound alone or as a pharmaceutical formulation.

11 Claims, No Drawings

HETEROCYCLIC CHEMICALS, THEIR PREPARATION AND USE

The present invention relates to novel nitrothiazoline compounds having schistosomicidal activity and/or value as chemical intermediates, to processes for their preparation, to pharmaceutical formulations containing them and to their use in medicine.

It is known from British patent specification No. 1,245,916 and U.S. Pat. No. 3,660,417 that nitrothiazolines of the following general formula (I) have schistosomicidal activity:

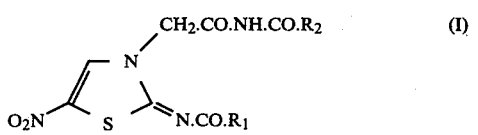

wherein $R_1$ is lower alkyl, lower alkoxy, cyclopropyl, phenyl or 2-thienyl, and $R_2$ is lower alkyl or cyclopropyl; the lower alkyl and lower alkoxy groups having not more than 4 carbon atoms. Compounds of formula (I) wherein $R_1$ is phenyl are exemplified in Example 2 of the above-identified specifications by 2-[2-(benzoylimino)-5-nitro-4-thiazolin-3yl]diacetamide, i.e. the phenyl ring is unsubstituted.

It is also known from British patent specification No. 1,158,751 and U.S. Pat. No. 3,499,907 that nitrothiazolines of the following general formula (II) have schistosomicidal activity:

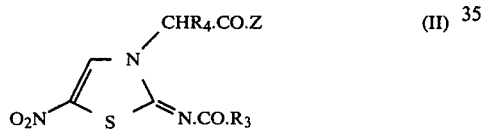

wherein $R_3$ is lower alkyl, cycloalkyl, phenyl, lower alkoxy or phenoxy, $R_4$ is hydrogen or methyl, and Z represents a lower alkoxy group or an amino group; the lower alkyl groups having not more than 6 carbon atoms, the lower alkoxy groups having not more than 4 carbon atoms, and the cycloalkyl groups having from 3 to 6 carbon atoms. Compounds wherein $R_3$ is phenyl are exemplified in Example 3(b) of the above-identified specifications by 2-(benzoylimino)-5-nitro-4-thiazoline-3-acetamide, i.e. the phenyl ring is again unsubstituted.

It has now unexpectedly been found that 2-(substituted-benzoylimino)-5-nitro-4-thiazolines of formula (III):

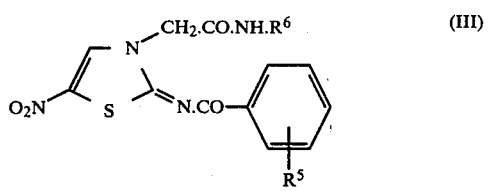

wherein $R^5$ is a single substituent in position 2 or 3 of phenyl ring and when in the 2-position $R^5$ is a chlorine atom, a methyl group or a nitro group and when in the 3-position $R^5$ is a nitro group; and $R^6$ is a hydrogen atom or a $CO.CH_3$ group possess a most effective activity against Schistosoma mansoni in, for example, mice and monkeys. The compounds of formula (III) also have a notably low level of toxicity to the host.

Preferred compounds of formula (III) are those wherein $R^6$ is $CO.CH_3$. Compounds of formula (III) which, as a result of their schistomicidal action and low toxicity, are particularly preferred are those of the following group:

2[2-(2-chlorobenzoylimino)-5-nitro-4-thiazolin-3-yl]diacetamide;
2[2-(2-nitrobenzoylimino)-5-nitro-4-thiazolin-3-yl]diacetamide;
2-[2-(3-nitrobenzoylimino)-5-nitro-4-thiazolin-3-yl]diacetamide; and
2-[2-(2-methylbenzoylimino)-5-nitro-4-thiazolin-3-yl]diacetamide.

Of the compounds wherein $R^6$ is a hydrogen atom, the preferred group comprises those compounds of formula (III) wherein $R^5$ is a methyl or a nitro group, and particularly preferred is 2-[(3-nitrobenzoyl)imino]-5-nitro-4-thiazoline-3-acetamide.

The compounds of formula (III) may be prepared by any method known in the art for the preparation of compounds of analogous structure.

For example, the compounds of formula (III) may be prepared by reacting a compound of formula (IV) with a compound of formula (V):

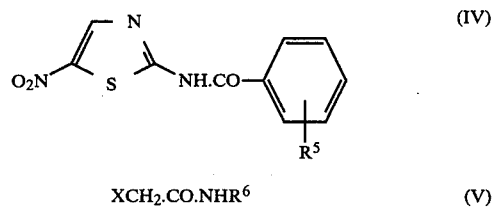

$$XCH_2.CO.NHR^6 \quad (V)$$

wherein $R^5$ and $R^6$ are as defined in formula (III) and X is a halogen atom, for example bromine or iodine.

The reaction may be performed in the presence of a base and/or a solvent. Bases that may be used include inorganic bases such as an alkali metal alkoxide for example sodium methoxide or an alkali metal carbonate for example sodium carbonate or preferably an alkali metal hydride especially sodium hydride. With the preferred base, a variety of non-hydroxylic solvents may be employed, including aprotic polar organic solvents, the preferred reaction solvent being N,N-dimethylformamide. The reaction may be effected at 0°–100°, although it is preferably carried out at from ambient temperature to 40° Celsius. Preferably, the reaction is effected with a slight excess (up to 20%) of base and haloalkylating agent.

The benzamide starting material of formula (IV) wherein $R^5$ is as defined in formula (III) may be conveniently prepared by benzoylating 2-amino-5-nitrothiazole preferably in the presence of an organic or inorganic base, for example a tri-(lower alkyl)amine or a heterocyclic base such as pyridine. The benzoylating agent may be an appropriate anhydride or acid halide, such as an acid chloride or acid bromide. Suitable solvents include non-reactive hydrocarbons, esters and ketones, although an excess of a suitable liquid tertiary amine may be employed. Whilst the reaction may be effected with equimolar amounts of 2-amino-5-nitrothiazole, benzoylating agents and base, it is preferable to use excess pyridine as both solvent and base. The reaction may be effected at 0°–100°, but is conveniently carried out at from 0° Celsius to ambient temperature.

The compounds of formula (III) wherein $R^6$ is $CO.CH_3$ may also be prepared by acylating the corresponding compound of formula (III) wherein $R^6$ is hydrogen, or vice versa.

Acylation may be effected by any method known in the art, for example, by using a reactive carboxylic acid derivative (i.e. $R^6.OH$ when $R^6$ is other than a hydrogen atom) desirably in the presence of an acid catalyst. Suitable reactive derivatives are acid anhydrides and halides preferably used in excess of equimolar amount, whilst any number of acid catalysts may be used including mineral acids, for example, hydrochloric, hydrobromic, nitric, sulphuric and phosphoric acids, and strongly acidic acids such as benzenesulphonic acid. A preferred acid catalyst is concentrated sulphuric acid. Typically the reaction is effected at 50°–200°, preferably 100°–120° Celsius.

The compounds of formula (III) (hereinafter referred to as the active compounds) are useful as anthelmintics and may be used to treat schistosome infections of mammals, especially schistosome infections of man, monkeys, cattle, sheep and rodents. The particular infections which may be treated are those of *S. mansoni, S. haematobium, S. japonicum, S. bovis* and *S. mattheei.*

The dose range of an active compound which is particularly suitable for effective anthelmintic use is dependent on the infected host species, the particular compound to be administered and is ultimately at the discretion of the physician. For example, a suitable dose may vary from 1 to 150 mg per kg body-weight of mammal per day, optionally as divided doses, for example two or three doses per day. The preferred dose range is from 1.5 to 100 mg per kg per day; more preferred is from 5 to 40 mg per kg per day; an optimal dose being 20 mg per kg per day.

In particular, for use in treating schistosomiasis in mammals such a man, monkeys, cattle and sheep, the active compound is administered orally or parenterally (that is, subcutaneously, intramuscularly, intraperitoneally or intravenously, preferably subcutaneously or intramuscularly and more preferably intramuscularly) most preferably orally.

A typical dose regime for man would be, for example, 3 times per day at a unit dose range of from 23.3 mg to 3.5 g; preferably from 35 mg to 2.3 g; more preferably from 116 mg to 930 mg; an optimal dose being 470 mg.

While it is possible for the active compound to be administered as a raw chemical, it is preferable to present the active compound as one or more pharmaceutical formulations.

A formulation of the present invention, both for veterinary and for human medical use, comprises an active compound together with one or more acceptable carriers therefor and optionally other therapeutic ingredient(s). The carrier must be 'acceptable' in the sense of being compatible with other ingredients of the formulation and not deleterious to the recipient therefor.

The formulation may conveniently be presented in unit dosage form and may be prepared by methods known in the art of pharmacy. All such methods include the step of bringing into association the active compound with the carrier which constitutes one or more accessory ingredients. In general the formulation is prepared by uniformly and intimately brining into association, e.g. by admixing, the active compound with a liquid carrier or a finely divided solid carrier or both, and then, if necessary, shaping the formulation into the desired presentation.

Formulations include those suitable for oral (e.g. buccal) or parenteral (including subcutaneous, intramuscular, intraperitoneal or intravenous injection or infusion).

A formulation according to the invention suitable for oral administration may be presented as a discrete unit such as a capsule, cachet, lozenge or tablet each containing a predetermined amount of the active compound as a powder or granules; or as a solution or a suspension in an aqueous or non-aqueous liquid; or as an oil-in-water emulsion or a water-in-oil liquid emulsion.

A tablet may be made by compression or moulding, optionally with one or more accessory ingredient(s). Compressed tablets may be prepared by compressing in a suitable machine the active compound in a free-flowing form, such as in micronized form or as a powder or as granules, optionally mixed with one or more excipients such a binding, dispersing or lubricating agents examples of which are, respectively, polyvinylpyrrolidone, pre-gelled starch, gelatin, cellulose and cellulose derivatives; sodium starch glycollate, calcium carboxymethyl cellulose and ion exchange resins; stearates, hydrogenated oils and talc. Other excipients include a pharmaceutically inert diluent and/or a surface active agent. Moulded tablets may be made by moulding in a suitable machine the active compound together with a suitable carrier moistened with a pharmaceutically inert liquid diluent.

Alternatively a compound of formula (III) may be dispersed in a melted hydrophilic carrier, the solution then being allowed to cool and solidify. Examples of such carriers are polyethylene glycol, polyvinylpyrrolidone, urea and organic acids such as succinic acid citric acids. The solid dispersion is then granulated and formed into tablets or filled into capsules as described above.

Suspensions of the compounds of formula (III) are another convenient form for oral presentation, and may be prepared using, as the excipients, suspending, preserving and flavouring agents. Suitable examples are Carbomer (British Pharmacopeia Codex), methyl hydroxybenzoate and any appropriate flavouring agent. The souble materials may be dissolved in water and the insoluble ones are then dispersed in the solution. Generally it is desirable that the acidity of the suspension is adjusted to within the range of pH 5 to 6.

Solubilizing agents may also be incorporated into the formulations suitable for oral administration.

Formulations for parenteral administration include those suitable for subcutaneous, intramuscular, intravenous and intraperitoneal administration, especially those suitable for subcutaneous or intramuscular administration, more especially the latter as shown in Example 16.

Parenteral forms for injection are essentially sterile and based on Water for Injections (British Pharmacopeia) or another similar standard. Dispersing, suspending and/or solubilising agents may be incorporated into the formulation.

A formulation according to the invention for parenteral administration may be presented in an ampoule for receiving a defined quantity of liquid for making a solution for infusion.

Solubilizing agents include arachis oil, maize oil, olive oil, glycofurol, PEG 400 (Trade Name), glycerol formal, dimethylsulphoxide, propylene glycol and Tween 80 (Trade Name); preferred agents for parenteral formulations are maize oil and glycofurol and especially maize oil for oral formulations, as shown in Example 16.

The present invention in its various aspects therefore provides:
(i) a nitrothiazoline of formula (III) as hereinbefore defined;
(ii) a process for the preparation of the compounds of formula (III) as hereinbefore described;
(iii) a pharmaceutical formulation comprising a compound of formula (III) in association with a pharmaceutically acceptable carrier therefor, and the preparation of such formulations;
(iv) a method for the treatment of an anthelmintic infection, especially a schistosome infection, of a mammal comprising administering to the mammal a non-toxic, effective schistosomidical amount of a compound of formula (III) or a pharmaceutical formulation thereof; or
(v) a nitrothiazoline of formula (III) for use in the treatment of an anthelmintic infection, especially a schistosome infection, of a mammal.

The invention will now be described, but by way of illustration only, with reference to the following Examples, in which all temperatures are indicated in degrees Celsius.

EXAMPLE 1

Preparation of
2-[2-(2-Methylbenzoylimino)-5-nitro-4-thiazolin-3-yl]diacetamide

A solution of o-toluoyl chloride (17 g) in a few milliliters of pyridine was added dropwise to a suspension of 2-amino-5-nitrothiazole (16 g) in pyridine (100 ml), initially at room temperature, then at 0°. After the addition was complete, the reaction mixture was stirred for 2 hr at room temperature, and was then quenched in ice-water. Recrystallisation of the precipitated amide from 2-methoxyethanol afforded 2-methyl-N-(5-nitro-2-thiazolyl)benzamide, m.pt. 228°–230°.

Sodium hydride in mineral oil dispersion (0.9 g 60% w/w) was added in portions to a suspension of 2-methyl-N-(5-nitro-2-thiazolyl)benzamide (5.3 g) in N,N-dimethylformamide (50 ml). When the evolution of hydrogen ceased, a solution of 2-bromodiacetamide (4.7 g) in N,N-dimethylformamide (20 ml) was added dropwise. The reaction mixture was stirred for 1 hr at room temperature (pH ca 7.0) and was then diluted with ice-water. Recrystallisation of the precipitated solid twice from industrial ethanol (SVM) produced 2-[2-(2-methylbenzoylimino)-5-nitro-4-thiazolin-3-yl]diacetamide, m.pt 226°–228°.

EXAMPLE 2

Preparation of
2-[2-(3-Nitrobenzoylimino)-5-nitro-4-thiazolin-3-yl]diacetamide

By following the procedure of the first part of Example 1, but using m-nitrobenzoyl chloride (27.8 g), 2-amino-5-nitrothiazole (21.8 g) and pyridine (100 ml), there was obtained 3-nitro-N-(5-nitro-2-thiazolyl)benzamide, m.pt 200°–201°, after recrystallisation from acetic acid.

By following the procedure of the second part of Example 1, but using sodium hydride in mineral oil dispersion (0.9 g, 60% w/w), 2-nitro-N-(5-nitro-2-thiazolyl)benzamide (5.9 g), N,N-dimethylformamide (120 ml) and 2-bromodiacetamide (4.7 g), there was obtained 2-[2-(3-nitrobenzoylimino)-5-nitro-4-thiazolin-3-yl]diacetamide, m.pt 234°–236°, after recrystallisation from pyridine.

EXAMPLE 3

Preparation of
2-[2-(2-Chlorobenzoylimino)-5-nitro-4-thiazolin-3-yl]diacetamide

By following the procedure of the first part of Example 1, but using 2-chlorobenzoyl chloride (26.3 g), 2-amino-5-nitrothiazole (21.8 g) and pyridine (ca 150 ml), there was obtained 2-chloro-N-(5-nitro-2-thiazolyl)benzamide, m.pt 221°–222°, after recrystallisation from acetic acid.

By following the procedure of the second part of Example 1, but using sodium hydride dispersion in mineral oil (0.8 g, 60% w/w), 2-bromodiacetamide (3.5 g), N,N-dimethylformamide (25 ml) and 2-chloro-N-(5-nitro-2-thiazolyl)-benzamide (5.1 g), there was obtained 2-[2-(2-chlorobenzoylimino)-5-nitro-4-thiazolin-3-yl]diacetamide, m.pt 229°–231°, after recrystallisation from acetic acid.

EXAMPLE 4

Preparation of
2-[2-(2-Nitrobenzoylimino)-5-nitro-4-thiazolin-3-yl]diacetamide

By following the procedure of the first part of Example 1, but using 2-nitrobenzoyl chloride (18.5 g), 2-amino-5-nitrothiazole (14.5 g) and pyridine (ca 80 ml), there was obtained 2-nitro-N-(5-nitro-2-thiazolyl)-benzamide, m.pt 248°–250°, after crystallization from 2-methoxyethanol.

By following the procedure of the second part of Example 1, but using sodium hydride dispersion in mineral oil (1.6 g, 60% w/w), 2-bromo-diacetamide (8.2 g), N,N-dimethylformamide (ca 70 ml) and 2-nitro-N-(5-nitro-2-thiazolyl)benzamide (10.3 g), there was obtained 2-[2-(2-nitrobenzoylimino)-5-nitro-4-thiazolin-3-yl]-diacetamide, m.pt 247°–249°, after recrystallization from acetic acid.

EXAMPLE 5

Preparation of
2-[(2-Methylbenzoyl)imino]-5-nitro-4-thiazoline-3-acetamide

Sodium hydride in mineral oil (2.1 g, 60% w/w) was added in portions to a stirred suspension of 2-methyl-N-(5-nitro-2-thiazolyl)benzamide (10.5 g) in N,N-dimethylformamide (100 ml). When the evolution of hydrogen ceased, 2-iodoacetamide (11.1 g) was added in portions. The mixture was stirred at room temperature for ca 1 hr., then poured into ice-water. Recrystallization of the separated solid from acetic acid afforded 2-[(2-methylbenzoyl)imino]-5-nitro-4-thiazoline-3-acetamide, m.pt 248°–250°.

EXAMPLE 6

Preparation of
2-[(3-Nitrobenzoyl)imino]-5-nitro-4-thiazoline-3-acetamide

By following the procedure of Example 5, but using a dispersion of sodium hydride (2.1 g 60% w/w) in mineral oil, 3-nitro-N-(5-nitro-2-thiazolyl)benzamide (11.8 g), N,N-dimethylformamide (100 ml) and 2-iodoacetamide (11.1 g), there was obtained 2-[(3-nitrobenzoyl)imino]-5-nitro-4-thiazoline-3-acetamide, m.pt 251°–252°, after recrystallization from pyridine.

EXAMPLE 7

Preparation of 2-[2-(2-Methylbenzoylimino)-5-nitro-4-thiazolin-3-yl]diacetamide

A mixture of 2-[(2-methylbenzoyl)imino]-5-nitro-4-thiazoline-3-acetamide (As prepared by Example 5) (6.4 g), acetic anhydride (50 ml) and concentrated sulphuric acid (5 drops) was heated for 2 hr at ca 100°, then left overnight at room temperature. Recrystallization of the separated solid from industrial ethanol (SVM) afforded a sample of 2-[2-(2-methylbenzoylimino)-5-nitro-4-thiazolin-3-yl]diacetamide identical with that prepared in Example 1.

EXAMPLE 8

Preparation of 2-[2-(3-Nitrobenzoylimino)-5-nitro-4-thiazolin-3-yl]diacetamide

By following the procedure of Example 7, but using 2-[(3-nitrobenzoyl)imino]-5-nitro-4-thiazoline-3-acetamide (7.0 g) (As prepared by Example 6), acetic anhydride (50 ml) and 5 drops of concentrated sulphuric acid, there was obtained a sample of 2-[2-(3-nitrobenzoylimino)-5-nitro-4-thiazolin-3-yl]diacetamide identical with that prepared in Example 2.

EXAMPLE A

Tablets containing 2-[2-(3-nitrobenzoylimino)-5-nitro-4-thiazolin-3-yl]diacetamide

| Ingredients | Weight per tablet |
| --- | --- |
| The diacetamide | 350 mg |
| Starch | 50 mg |
| Polyvinylpyrrolidone | 2 mg |
| Magnesium stearate | 2 mg |

The diacetamide is mixed with the starch and granulated with the polyvinylpyrrolidone dissolved in water. The granules are dried at 50°, then sifted 1000 μm and mixed with the magnesium stearate. The mixture is then compressed into tablets each weighing 400 mg.

EXAMPLE B

Capsules containing 2-[2-(3-nitrobenzoylimino)-5-nitro-4-thiazolin-3-yl]diacetamide (a) The granules prepared in Example 9 and mixed with the stearate are filled into hard gelatin capsules each containing 404 mg of the mixture.

(b)

| Ingredients | Weight per capsule |
| --- | --- |
| The diacetamide | 175 mg |
| Polyethylene glycol 4000 | 325 mg |
| Magnesium stearate | 2 mg |

The glycol is melted and micronised diacetamide is added. After cooling the mixture is ground and passed through a 1000 μm sieve. The magnesium stearate is added and mixed in, and the whole is filled into hard gelatin capsules.

EXAMPLE C

Dispersible tablet containing 2-[2-(3-nitrobenzoylimino-5-nitro-4-thiazolin-3-yl]diacetamide

| Ingredients | Weight per tablet |
| --- | --- |
| The diacetamide | 675 mg |
| Sodium starch glycollate | 70 mg |
| Microcrystalline cellulose | 100 mg |
| Polyvinylpyrrolidone | 10 mg |
| Dioctyl sodium sulphosuccinate | 0.5 mg |
| Starch | 70.0 mg |
| Magnesium stearate | 5.5 mg |

Micronised diacetamide is mixed with the sodium starch glycollate and the starch, and the mixture is granulated with the polyvinylpyrrolidone and the sulphosuccinate in 50% v/v alcohol. The granules are dried, sifted 1000 μm and mixed with the cellulose and the stearate. Compression then produces tablets weighing 931 mg each.

EXAMPLE D

Oral suspension of 2-[2-(3-nitrobenzoylimino)-5-nitro-4-thiazolin-3-yl]diacetamide

| Ingredients | Amount per 100 ml |
| --- | --- |
| The diacetamide | 10.00 g |
| Carbomer B.P.C, 1976 supplement | 0.60 g |
| 1 M Sodium hydroxide | q.s. to pH 5–6 |
| Methyl hydroxybenzoate | 0.10 g |
| Sucrose | 45.00 g |
| Flavouring agent | q.s. |
| Purified Water B.P. to | 100.00 ml |

The carbomer, which acts as a suspending an viscosity binding agent, is dispersed in a solution of the methylhydroxybenzoate in 65 ml of the Purified Water. The sucrose is added and dissolved with high speed stirring of the solution, and the diacetamide is then added and dispersed. The pH of the dispersion is adjusted to the desired range of 5 to 6 by addition of the sodium hydroxide, during this stage the suspension thickens. The flavouring agent is incorporated with gentle stirring, and the volume is adjusted by using further Purified Water.

EXAMPLE E

Injectable suspension of 2-[2-(3-nitrobenzoylimino)-5-nitro-4-thiazolin-3-yl]diacetamide

| Ingredients | Amount per ml |
| --- | --- |
| Micronised diacetamide | 125 mg |
| Polysorbate 80 (wetting/dispersing agent) | 5 mg |
| Methyl hydroxybenzoate (preservative) | 10 mg |
| Water for Injections B.P. to | 1.00 ml |

The hydroxybenzoate is dissolved in 0.8 ml of Water for Injections, British Pharmacopoeia standard (B.P.), at 80° and the solution is allowed to cool. The polysorbate is added, and this solution is sterilised by passage through a membrane filter, 0.22 μm pore size, the filtrate being collected in a sterile receiver. Under aseptic conditions the diacetamide, previously sterilised by gamma-irradiation, is added and dispersed using a high shear mixer. The suspension is diluted to the required volume using sterile Water for Injections, B.P. and filled into sterilised 2 ml or 3 ml glass vials. These are sealed with a sterile rubber closure.

EXAMPLE F

Further pharmaceutical compositions

Tablets, capsules, dispersible tablets, oral suspensions and injectable suspensions similar to those in respectively Examples A to E are prepared using, instead of the 3-nitrobenzoyliminodiacetamide, the following compounds:
 (i) 2-[2-(2-nitrobenzoylimino)-5-nitro-4-thiazolin-3-yl]-diacetamide;
 (ii) 2-[2-(2-methylbenzoylimino)-5-nitro-4-thiazolin-3-yl]diacetamide;
 (iii) 2-[2-(3-nitrobenzoyl)imino]-5-nitro-4-thiazolin-3-acetamide

EXAMPLE I

Schistosomicdal Activity of compounds of formula (III)

Male mice weighing between 18 and 20 g were each infected percutaneously with 80 to 100 cercariae of *Schistosoma mansoni*. Groups of 5 or 10 mice with a 7 to 9 week infection of schistosomes were dosed orally (P.O.) or subcutaneously (S.C.) with 12.5 mg/kg of the compounds to be tested, and the animals were autopsied from 7 to 10 days after treatment. The number, sex and proportional distribution of schistosomes within the mesenteric, portal and intrahepatic veins were determined, and the final assessment of dose response was made on the proportion of dead worms found in relation to the total worms recovered in the treated group.

The results for compounds of formula (III) were as follows:

(a) Compounds wherein $R^6$ is $CO.CH_3$, i.e. diacetamides:

| Compound of Example | $R^5$ | % kill P.O. | % kill S.C. |
|---|---|---|---|
| 1 | 2-CH$_3$ | 80 | 100 |
| 2 | 3-NO$_2$ | 100 | 100 |
| 3 | 2-Cl | 100 | 99 |
| 4 | 2-NO$_2$ | 74 | 98 |
| *(1) | H | 58 | 53 |

*(1) This compound is described in British Patent Specification No 1 245 916 and U.S. Pat. Specification No. 3 660 417.

(b) Compounds wherein $R^6$ is a hydrogen atom, i.e. acetamides:

| Compound of Example | $R^5$ | % kill P.O. | % kill S.C. |
|---|---|---|---|
| 3 | 3-NO$_2$ | 71 | 98 |
| *(2) | H | 8.5 | 0 |

*(2) This compound is described in British Patent Specification No 1 158 751 and U.S. Pat. Specification No. 3 499 907.

EXAMPLE II: Schistosomicidal activity of Compound of Example 1

A comparison was made of the schistosomicidal activity of the compound of Example 1 administered by different routes and using different formulations. The formulation were tested against mature *S. mansoni* in patas monkeys as indicated in the table. The assessment of the schistosomicidal effect of each formulation was based on the hatching of viable eggs from the faeces during a follow-up period of from 4 to 6 weeks from administration. 'Clinical cure' represents no viable eggs present in the faeces during the follow-up period.

'Virtual cure' represents from 90 to 99% absence of viable eggs in the faeces during the follow-up period.

| Dose mg/kg × no. of doses administered | Route of Administration | Carrier | Schistosomicidal Effect |
|---|---|---|---|
| 12.5 × 4 (at 1½ hour intervals) | Orally | Suspension in Gum tragacanth and water | Virtual cure of 2 of 4 monkeys |
| 12.5 × 4 (at 1½ hour intervals) | Orally | Suspension in 100% maize oil | Clinical cure of 2 of 2 monkeys |
| 25 × 1 | Intramuscularly | Suspension in 100% maize oil | Clinical cure 1 monkey |
| 25 × 1 | Subcutaneously | Suspension in 100% maize oil | Clinical cure 1 monkey |
| 25 × 1 | Intramuscularly | Solution in 100% glycofurol | Clinical cure 1 monkey |
| 25 × 1 | Subcutaneously | Solution in 100% glycofurol | Virtual cure 1 monkey |

EXAMPLE III: Toxicities of compounds of formula (III)

Groups of adult male mice were given graded doses of the compound to be tested by stomach tube (P.O.) or subcutaneously (S.C.). The animals were kept under observation at frequent intervals up to 6 hours, then at 24 hours and daily for up to 10 days for overt changes in behaviour and for fatalities. LD$_{50}$ values were calculated and were as follows:

| Compound of Example | $R^5$ | $R^6$ | LD$_{50}$P.O. | LD$_{50}$S.C. |
|---|---|---|---|---|
| 1 | 2-CH$_3$ | CO.CH$_3$ | >2000mg/kg | >2000mg/kg |
| 2 | 3-NO$_2$ | CO.CH$_3$ | >2000mg/kg | >2000mg/kg |
| 5 | 2-CH$_3$ | H | >2000mg/kg | >1000mg/kg |
| 6 | 3-NO$_2$ | H | >1000mg/kg | >500mg/kg |
| *(1) | H | CO.CH$_3$ | 953mg/kg | (I.V. = 192mg/kg) |
| *(2) | H | H | | |

*(1) This compound is described in British Patent Specification No 1 245 916 and U.S. Pat. Specification No. 3 660 417.

*(2) This compound is described in British Patent Specification No 1 158 751 and U.S. Pat. Specification No. 3 499 907.

We claim:
1. A compound of formula (III)

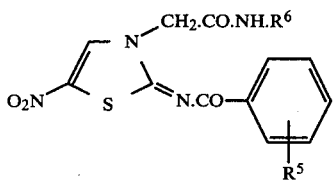

wherein
R⁵ is a single substituent substituted in a position of the phenyl ring selected from position 2 and position 3 and when in the 2-position R⁵ is selected from a chlorine atom, a methyl group and a nitro group and when in the 3-position R⁵ is a nitro group; and
R⁶ is selected from a hydrogen atom and a CO.CH₃ group.

2. A compound according to claim 1 wherein R⁶ is CO.CH₃.

3. A compound according to claim 2, selected from the group consisting of
2-[2-(2-chlorobenzoylimino)-5-nitro-4-thiazolin-3-yl]diacetamide;
2-[2-(2-nitrobenzoylimino)-5-nitro-4-thiazolin-3-yl]diacetamide;
2-[2-(3-nitrobenzoylimino)-5-nitro-4-thiazolin-3-yl]diacetamide; and
2-[2-(2-methylbenzoylimino)-5-nitro-4-thiazolin-3-yl]diacetamide.

4. A compound according to claim 1 wherein R⁶ is a hydrogen atom.

5. A compound according to claim 4, selected from the group consisting of
2-[(2-methylbenzoyl)imino]-5-nitro-4-thiazoline-3-acetamide;
2-[(3-nitrobenzoyl)imino]-5-nitro-4-thiazoline-3-acetamide;
2-[(2-chlorobenzoyl)imino]-5-nitro-4-thiazoline-3-acetamide; and
2-[(2-nitrobenzoyl)imino]-5-nitro-4-thiazoline-3-acetamide.

6. A pharmaceutical formulation comprising a non-toxic effective schistosomal amount of the compound of claim 1 in association with a pharmaceutically acceptable carrier therefor.

7. A pharmaceutical formulation according to claim 6 wherein the carrier is selected from maize oil and glycofurol.

8. A pharmaceutical formulation according to claim 6 or claim 7 wherein the compound of formula (III) is 2-[2-(2-methylbenzoylimino)-5-nitro-4-thiazolin-3-yl]diacetamide.

9. A method for the treatment of a schistosome infection of a mammal comprising administering to the mammal a non-toxic, effective schistosomicidal amount of a compound as defined in claims 1 to 5.

10. A method according to claim 9 wherein the infection is selected from the group consisting of *S. mansoni, S. haematobium, S. japonicum, S. bovis* and *S. mattheei*.

11. A method according to claim 9 wherein the compound of formula (III) is in association with an acceptable carrier therefor.